United States Patent
Prencipe et al.

(10) Patent No.: US 10,052,270 B2
(45) Date of Patent: *Aug. 21, 2018

(54) PEROXIDE-STABLE ORAL CARE COMPOSITIONS

(71) Applicant: Colgate-Palmolive Company, Piscataway, NJ (US)

(72) Inventors: Michael Prencipe, West Windsor, NJ (US); Prakasarao Mandadi, Flemington, NJ (US); Olivier Garot, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,655

(22) PCT Filed: Dec. 14, 2012

(86) PCT No.: PCT/US2012/069867
§ 371 (c)(1),
(2) Date: Jun. 11, 2015

(87) PCT Pub. No.: WO2014/092735
PCT Pub. Date: Jun. 19, 2014

(65) Prior Publication Data
US 2015/0366766 A1  Dec. 24, 2015

(51) Int. Cl.
| | |
|---|---|
| A61K 8/22 | (2006.01) |
| A61Q 11/00 | (2006.01) |
| A61K 8/86 | (2006.01) |
| A61K 31/79 | (2006.01) |
| A61K 8/24 | (2006.01) |
| A61K 8/81 | (2006.01) |
| A61K 8/25 | (2006.01) |
| A61K 8/34 | (2006.01) |

(52) U.S. Cl.
CPC .............. *A61K 8/22* (2013.01); *A61K 8/24* (2013.01); *A61K 8/25* (2013.01); *A61K 8/345* (2013.01); *A61K 8/8176* (2013.01); *A61K 8/86* (2013.01); *A61Q 11/00* (2013.01); *A61K 2800/28* (2013.01); *A61K 2800/57* (2013.01)

(58) Field of Classification Search
CPC . A61K 8/345; A61K 8/22; A61K 8/24; A61K 8/8176; A61K 8/86; A61Q 11/00
USPC ...................................... 424/49, 53
See application file for complete search history.

(56) References Cited

U.S. PATENT DOCUMENTS

| | | | |
|---|---|---|---|
| 5,776,435 A | 7/1998 | Gaffar et al. | |
| 2003/0082114 A1 * | 5/2003 | Kim .................. | A61K 8/0208 424/53 |
| 2005/0036956 A1 | 2/2005 | Fei et al. | |
| 2005/0063923 A1 | 3/2005 | Prencipe et al. | |
| 2006/0045854 A1 | 3/2006 | Zaidel et al. | |
| 2006/0062744 A1 | 3/2006 | Lokken | |
| 2008/0014224 A1 | 1/2008 | Boyd et al. | |
| 2008/0193392 A1 | 8/2008 | Kwak et al. | |
| 2015/0320649 A1 | 11/2015 | Maloney et al. | |
| 2015/0328092 A1 | 11/2015 | Fei et al. | |

FOREIGN PATENT DOCUMENTS

| | | |
|---|---|---|
| GB | 1209319 A | 10/1970 |
| JP | 2003-526648 | 9/2003 |
| JP | 2007-515385 | 6/2007 |
| WO | WO 2007/037961 A1 | 4/2007 |
| WO | WO 2011/079167 A2 | 6/2011 |
| WO | WO 2012/102750 A1 | 8/2012 |
| WO | WO 2012/166142 | 12/2012 |

OTHER PUBLICATIONS

International Search Report and Written Opinion for International Application No. PCT/US2012/069867 dated Oct. 17, 2013.

* cited by examiner

*Primary Examiner* — Lezah Roberts

(57) ABSTRACT

Described herein are oral care compositions comprising (i) a peroxide whitening agent comprising a whitening complex of crosslinked polyvinylpyrrolidone complexed with hydrogen peroxide, (ii) sodium acid pyrophosphate ($Na_2H_2P_2O_7$) in an amount of from 0.05 wt % to 5 wt % based on the weight of the composition, and (iii) less than 3 wt % water based on the weight of the composition.

19 Claims, No Drawings

PEROXIDE-STABLE ORAL CARE COMPOSITIONS

BACKGROUND

Dentifrice formulations comprising peroxide are known and useful for cleaning and whitening teeth. The peroxide can bleach the teeth, remove stains, and kill cardiogenic bacteria. However, peroxide compounds are highly reactive, and consequently difficult to formulate. Moreover, hydrogen peroxide can spontaneously decompose to form oxygen gas ($O_2$) and water, so that on storage, the dentifrice containers may bloat, burst or leak, and the remaining formulation will not have enough peroxide remaining to clean and whiten teeth effectively. Some initially comprise very high levels of peroxide, which decomposes over time, so that the exact amount of peroxide delivered on application is variable and largely depends on how long and under what conditions the dentifrice has been stored.

The peroxide may be present as hydrogen peroxide or as a source of bound hydrogen peroxide. Sources of bound hydrogen peroxide include PVP—$H_2O_2$ complexes, urea peroxide, calcium peroxide and sodium percarbonate.

Hydrogen peroxide and such sources of bound hydrogen peroxide are challenging to formulate into stable dentifrice products due to their reactivity with many common ingredients found in oral care products, especially water and abrasives. It is known in the art that peroxide stability can be improved by decreasing the formula pH. However, lowering the pH below 5.5, or even below an optimal minimum threshold of pH 6 when used in aqueous solution during brushing, in toothpaste designed to be used daily could lead to harmful erosion of enamel.

Single phase whitening dentifrice compositions are described, for example, in the Applicant's earlier WO-A-2012/102750, WO-A-2011/079167 and WO-A-2007/037961, and in US-A-2006/0062744, the contents of which are incorporated herein by reference. Those compositions are not acidic and comprise PVP—$H_2O_2$ complexes which stabilize the hydrogen peroxide in the composition, which has a low water content or is substantially anhydrous. By exposure to aqueous environments, as in the oral cavity, the PVP—$H_2O_2$ dissociates into individual species (PVP polymer and $H_2O_2$). The PVP—$H_2O_2$ complex is generally comprised of about 80% by weight polyvinyl pyrrolidone and 20% by weight $H_2O_2$. It has also been demonstrated in WO-A-2012/102750 that the careful selection of a calcium abrasive and an ethylene oxide, propylene oxide block co-polymer of a specific molecular weight can also be used to improve the stability of bound hydrogen peroxide in dentifrice.

However, known whitening dentifrice compositions including peroxide may exhibit an unacceptable level of peroxide decomposition and loss of whitening efficacy as a result of being stored prior to sale or by the user.

There is thus a need for improved peroxide-containing whitening oral care compositions, for example dentifrice compositions, which exhibit improved cosmetic stability of the peroxide, and so are chemically stable for long-term storage and are suitable for everyday consumer use without significant loss of whitening efficacy.

Furthermore, when formulating oral care compositions, for example dentifrice compositions, it is important that the formulation has physical stability and does not progressively separate into solid and liquid phases as a result of being stored prior to sale or by the user. Some known whitening dentifrice compositions including peroxide may exhibit a significant level of phase separation, which is unacceptable to the user.

There is thus a further need for improved peroxide-containing whitening oral care compositions, for example single phase dentifrice compositions, which exhibit improved cosmetic phase stability of the composition, and so are physically stable for long-term storage and are suitable for everyday consumer use without significant breakdown of the single phase.

SUMMARY

The invention at least partly aims to meet either or both of those needs.

The invention also aims to provide a single phase whitening oral care composition, which exhibits cosmetic chemical stability of the peroxide and physical stability of the composition, and so is chemically and physically stable for long-term storage and is suitable for everyday consumer use, and remains effective to clean and whiten teeth.

The invention further aims to provide a single phase whitening oral care composition, which exhibits acceptable pH during use, for example greater than pH 6, and sufficiently low viscosity to be extrudable by the consumer and pumpable during manufacture.

Accordingly, the invention provides an oral care composition comprising (i) a peroxide whitening agent comprising a whitening complex of crosslinked polyvinylpyrrolidone complexed with hydrogen peroxide, (ii) sodium acid pyrophosphate ($Na_2H_2P_2O_7$) in an amount of from 0.05 wt % to 5 wt % based on the weight of the composition, and (iii) less than 3 wt % water based on the weight of the composition.

Optionally, the sodium acid pyrophosphate ($Na_2H_2P_2O_7$) is present in an amount of from 0.1 wt % to 5 wt % based on the weight of the composition, further optionally from 0.1 wt % to 3 wt % based on the weight of the composition.

Optionally, the whitening complex of crosslinked polyvinylpyrrolidone complexed with hydrogen peroxide is present in an amount of from 3 wt % to 15 wt %, further optionally from 5 wt % to 12 wt %, based on the weight of the composition.

Optionally, the whitening complex contains 10-30 wt % hydrogen peroxide and 5-15 wt % total nitrogen, based on the weight of the whitening complex. Optionally, the total amount of hydrogen peroxide is from 0.5 wt % to 3 wt % based on the weight of the composition.

Optionally, the composition further comprises a tartar control agent selected from tetrasodium pyrophosphate and sodium tripolyphosphate or a mixture thereof. Further optionally, the tartar control agent comprises from 1 to 2 wt % tetrasodium pyrophosphate based on the weight of the composition.

Optionally, the composition further comprises an abrasive selected from at least one of calcined alumina, silica, zirconium oxide, calcium pyrophosphate, dicalcium phosphate and precipitated calcium carbonate, or any mixture of two or more thereof. Typically, the abrasive is present in an amount of from 5 wt % to 40 wt % based on the weight of the composition. Optionally, the abrasive is calcium pyrophosphate present in an amount of from 12 wt % to 37 wt % based on the weight of the composition.

In some embodiments, the composition further comprises at least one humectant selected from glycerin and propylene glycol, or a mixture thereof. Optionally, the at least one humectant is present in an amount of from 25 wt % to 60 wt % based on the weight of the composition, further optionally from 25 wt % to 45 wt % based on the weight of the composition. In some embodiments, the composition comprises propylene glycol in an amount of from 15 wt % to 30 wt % based on the weight of the composition. In some embodiments, the composition comprises glycerin in an amount of from 5 wt % to 20 wt % based on the weight of the composition.

In some embodiments, the composition further comprises an ethylene oxide, propylene oxide block co-polymer of average molecular weight greater than 5000 Da, being substantially free of an ethylene oxide, propylene oxide block co-polymer of average molecular weight less than 5000 Da. Typically, the ethylene oxide, propylene oxide block co-polymer comprises (ethylene oxide)$_x$-(propylene oxide)$_y$, wherein x is an integer of 80-150 and y is an integer 30-80. Optionally, the ethylene oxide, propylene oxide block co-polymer is present in an amount of from 5 wt % to 12 wt % based on the weight of the composition.

In some embodiments, the composition further comprises polyethylene glycol of average molecular weight 400 to 800 Da. Optionally, the polyethylene glycol is present in an amount of from 5 wt % to 15 wt % based on the weight of the composition.

Optionally, the composition further comprises a thickening agent selected from crosslinked polyvinylpyrrolidone and fumed silica or a mixture thereof. Typically, the thickening agent is present in an amount of from 1 wt % to 5 wt % based on the weight of the composition.

Optionally, the composition contains less than 1 wt % water based on the weight of the composition.

Optionally, the composition is a single phase composition.

In some embodiments, the composition further comprises an anionic surfactant in an amount of from 0.5 to 3 wt % based on the weight of the composition.

In the preferred embodiments of the invention, the oral care compositions are chemically and physically stable during long term storage and remain effective to clean and whiten teeth, with good cosmetic stability during manufacture and use of the compositions.

The inventors have unexpectedly found that sodium acid pyrophosphate ($Na_2H_2P_2O_7$), otherwise referred to as SAPP or disodium pyrophosphate, can increase both the chemical peroxide stability and the physical phase stability in dentifrice including a peroxide whitening agent in the form of a whitening complex, particularly an anhydrous dentifrice, most particularly a single phase dentifrice. The amount of the sodium acid pyrophosphate ($Na_2H_2P_2O_7$) may be controlled so as not excessively to decrease the pH of the composition when used in an aqueous solution to brush the teeth and so as not excessively to increase the viscosity of the dentifrice so as to make it difficult to extrude from a package such as a tube or to pump during manufacture.

The invention also provides a method of tooth whitening comprising applying the composition of the invention to the surface of a mammalian tooth.

Further embodiments of the invention will be apparent from the detailed description and the examples.

DETAILED DESCRIPTION

As used throughout, ranges are used as shorthand for describing each and every value that is within the range. Any value within the range can be selected as the terminus of the range.

In some embodiments, the present invention provides an oral care composition comprising (i) a peroxide whitening agent comprising a whitening complex of crosslinked polyvinylpyrrolidone complexed with hydrogen peroxide, (ii) sodium acid pyrophosphate ($Na_2H_2P_2O_7$) in an amount of from 0.05 wt % to 5 wt % based on the weight of the composition, and (iii) less than 3 wt % water based on the weight of the composition.

The oral care composition typically is a single phase composition, for example a toothpaste.

In the oral care composition the whitening agent comprises a peroxide whitening complex which acts as a source of bound hydrogen peroxide, particular a PVP—$H_2O_2$ complex.

In some embodiments, the crosslinked polyvinylpyrrolidone complexed with hydrogen peroxide is present in an amount of from 3 wt % to 15 wt %, typically 5 wt % to 12 wt %, based on the weight of the composition.

Typically, the whitening complex contains 10-30 wt % hydrogen peroxide and 5-15 wt % total nitrogen, based on the weight of the whitening complex. In some embodiments, the total amount of hydrogen peroxide is from 0.5 wt % to 3 wt % based on the weight of the composition, e.g., 0.75-1.5 wt %, e.g. about 1 wt %.

Typically, the whitening complex contains about 15-25%, for example about 17-22% of hydrogen peroxide by weight, and about 7-12% total nitrogen by weight; for example, having substantially the same specification as Polyplasdone® XL-10, e.g., Polyplasdone® XL-10F, e.g., available from International Specialty Products (Wayne, N.J.).

In accordance with the invention sodium acid pyrophosphate ($Na_2H_2P_2O_7$) is present in an amount of from 0.05 wt % to 5 wt % based on the weight of the composition, and has been found to act as both a peroxide stabilizer and a phase stabilizer.

With such a peroxide stabilizer for the peroxide whitening agent, the whitening agent has reduced chemical decomposition. With such a phase stabilizer, the composition has reduced tendency to separate into solid and liquid phases.

In some embodiments, the sodium acid pyrophosphate ($Na_2H_2P_2O_7$) is present in an amount of from 0.1 wt % to 5 wt % based on the weight of the composition, typically from 0.1 wt % to 3 wt % based on the weight of the composition.

In some embodiments, the composition includes a thickening system in which a thickening agent, such as crosslinked polyvinvlpyrrolidone and/or fumed silica, is provided which thickens the composition to enable the composition to be extruded by a user from a container such as a tube to enable the composition to be used as a toothpaste or gel, and to be readily manufactured, in particular so as to be pumpable.

In some embodiments, the crosslinked polyvinvlpyrrolidone and/or fumed silica thickening agent is present in an amount of from 1 wt % to 5 wt %, based on the weight of the composition.

The compositions of the invention may optionally comprise an additional orally acceptable thickening agent, selected from one or more of, without limitation, carbomers, also known as carboxyvinyl polymers, carrageenans, also known as Irish moss and more particularly carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt %, based on the weight of the composition.

In some embodiments, the composition further comprises polymer thickeners selected from (i) polyethylene glycol, (ii) polyethylene glycol-polypropylene glycol block co-polymers having a molecular weight of at least 5000, and (iii) combinations thereof.

In some embodiments, the composition comprises an ethylene oxide, propylene oxide block co-polymer of formula (ethylene oxide)$_x$-(propylene oxide)$_y$, wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800;

In some embodiments, the composition comprises an ethylene oxide, propylene oxide block co-polymer of average molecular weight greater than 5000 Da, being substantially free of an ethylene oxide, propylene oxide block co-polymer of average molecular weight less than 5000 Da. Optionally, the ethylene oxide, propylene oxide block co-polymer is present in an amount of from 5 wt % to 12 wt % based on the weight of the composition. Block copolymers of ethylene oxide/propylene oxide are useful, but higher molecular weight, e.g., >5000 Da are preferred, e.g. including PLURACARE® L1220 (available from BASF, Wyandotte, Mich., United States of America).

In some embodiments, the composition further comprises polyethylene glycol of average molecular weight 400 to 800 Da, e.g., about 600 Da. Low or medium molecular weight polyethylene glycol, e.g., PEG 400, PEG 600, PEG 800, PEG 1000 and mixtures thereof are useful in the compositions of some embodiments of the invention.

Further optionally, the polyethylene glycol may be present in an amount of from 5 wt % to 15 wt % based on the weight of the composition.

In some embodiments, the oral care compositions may additionally comprise a stabilizing amount of an additional linear polyvinylpyrrolidone.

The compositions of the invention may also comprise various dentifrice ingredients to adjust the rheology and feel of the composition such as humectants, surface active agents, or gelling agents, etc.

In some embodiments, the oral care composition comprises a vehicle for the active components. The vehicle may comprise humectants, e.g. selected from glycerin, propylene glycol or a combination thereof.

In some embodiments, the oral care composition comprises from about 25 to about 60 wt %, optionally from about 25 to about 45 wt % humectant based on the weight of the composition.

In some embodiments, the composition further comprises propylene glycol in an amount of from 15 wt % to 30 wt % based on the weight of the composition.

In some embodiments, the composition further comprises glycerin in an amount of from 5 wt % to 20 wt % based on the weight of the composition.

Typical compositions of the invention have a "low water" content, meaning that a total concentration of water, including any free water and all water contained in any ingredients, is less than about 5 wt %, preferably less than 3 wt %, preferably less than 2 wt % water.

Optionally, the composition contains less than 3 wt % water based on the weight of the composition. In some embodiments, the oral care composition contains less than 2 wt % water, e.g., less than 1 wt % water. In some embodiments, the composition is substantially anhydrous.

It is preferred that the vehicle ingredients in particular provide a dentifrice with a viscosity of about 10,000 CPS to about 700,000 CPS, preferably about 30,000 CPS to about 300,000 CPS.

As recognized by one of skill in the art, the oral compositions of the invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

In some embodiments, the composition may additionally comprise an anionic surfactant, e.g., sodium lauryl sulfate (SLS). In some embodiments, the composition further comprises an anionic surfactant in an amount of from 0.5 to 3 wt % based on the weight of the composition.

The oral care composition may comprise an abrasive in the form of particles.

The abrasive is typically selected from at least one of calcined alumina, silica, zirconium oxide, calcium phosphate, calcium pyrophosphate, dicalcium phosphate dicalcium orthophosphate, tricalcium phosphate, calcium polymetaphosphate, and precipitated calcium carbonate, or any mixture of two or more thereof.

Typically, the coated abrasive is present in an amount of from 5 wt % to 40 wt %, more typically from 12 wt % to 37 wt % when the abrasive is calcium pyrophosphate, based on the weight of the composition.

The average abrasive particle size is generally about 0.1 to about 30 microns, for example about 1 to about 20 microns or about 5 to about 15 microns.

The compositions of the present invention optionally comprise one or more further active material(s), which is or are operable for the prevention or treatment of a condition or disorder of hard or soft tissue of the oral cavity, the prevention or treatment of a physiological disorder or condition, or to provide a cosmetic benefit.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition.

Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. Typically, the anticalculus agent is present at about 0.1% to about 30 wt % based on the weight of the composition.

The oral composition may include a mixture of different anticalculus agents.

In some embodiments, the composition additionally comprises a tartar control agent, e.g., selected from tetrasodium pyrophosphate (TSPP) and sodium tripolyphosphate (STPP).

In one preferred embodiment, tetrasodium pyrophosphate (TSPP) and/or sodium tripolyphosphate (STPP) are used. The anticalculus agent may comprise TSPP at about 1-2% and/or STPP at about 7% to about 10%, each based on the weight of the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions, each based on the weight of the composition.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%, each based on the weight of the composition.

In some embodiments, the compositions of the invention optionally comprise an antimicrobial (e.g., antibacterial) agent, e.g., triclosan. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%, each based on the weight of the composition.

In some embodiments, the compositions of the invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the invention may optionally comprise a sialagogue or saliva-stimulating agent, an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

Methods are provided to whiten an oral surface in a human or animal subject comprising storing in stable form a composition of the invention, and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with particular embodiments of the invention, is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The invention is illustrated in the following non-limiting examples.

EXAMPLES

Example 1 and Comparative Example 1

Dentifrice compositions were prepared according to each of Example 1 and Comparative Example 1. The compositions had the following ingredients as specified in Table 1, in which the amounts are in wt %:

TABLE 1

| Ingredient | Comp. Ex. 1 | Example 1 |
|---|---|---|
| $PEG_{118}/PPG_{66}$ co-polymer (Pluracare L1220F) | 10 | 10 |
| Glycerin | 5 | 5 |
| Propylene glycol | 25 | 24.9 |
| PEG 600 | 10 | 10 |
| Fumed silica | 1.5 | 1.5 |
| Crosslinked $PVP/H_2O_2$ complex | 5.5 | 5.5 |
| Tetrasodium pyrophosphate (TSPP) | 2 | 2 |
| Sucralose | 0.05 | 0.05 |
| Sodium saccharin | 0.6 | 0.6 |
| Sodium monofluorophosphate | 0.76 | 0.76 |
| Sodium lauryl sulfate | 2 | 2 |
| Butylated hydroxytoluene (BHT) | 0.03 | 0.03 |
| 85 wt % syrupy phosphoric acid | 0.2 | 0.2 |
| Flavor | 2.25 | 2.25 |
| Calcium pyrophosphate | 35.11 | 35.11 |
| Sodium acid pyrophosphate | — | 0.1 |
| Total | 100 | 100 |

The dentifrice of Comparative Example 1 comprised a peroxide whitening agent comprising a complex of crosslinked polyvinylpyrrolidone and hydrogen peroxide. The hydrogen peroxide comprised about 1 wt % of the total weight of the dentifrice. The dentifrice comprised a substantially anhydrous vehicle comprising $PEG_{118}/PPG_{66}$ copolymer (Pluracare L1220F), glycerin, propylene glycol and PEG 600. Fumed silica was present as a thickener and viscosity modifying agent. The abrasive comprised calcium pyrophosphate.

The dentifrice of Example 1 additionally comprised sodium acid pyrophosphate in an amount of 0.1 wt %.

The stability of the dentifrices of Example 1 and Comparative Example 1 was evaluated using two different testing protocols.

One testing protocol evaluated the chemical stability of hydrogen peroxide in the dentifrice and in particular evaluated the bloating of the packaging containing the dentifrice comprising the hydrogen peroxide.

The other testing protocol evaluated the physical stability of the dentifrice and in particular evaluated the phase separation of the dentifrice comprising the hydrogen peroxide.

Hydrogen peroxide chemically decomposes into the decomposition products of water and oxygen gas, with two moles of hydrogen peroxide producing one mole of oxygen. However, one mole of oxygen gas takes up more volume than 2 moles of hydrogen peroxide and so significant pressure can build up in a closed tube of dentifrice as hydrogen peroxide chemically degrades.

In the testing of Example 1 and Comparative Example 1, a conventional flexible polymer toothpaste tube having a shoulder width of 38 mm and a length of 125 mm was filled with 110 g of the respective dentifrice and the tube was closed with a conventional closure.

In the first testing protocol to evaluate the chemical stability of hydrogen peroxide in the dentifrice, the progressive bloating of the hydrogen peroxide-containing dentifrice formula of Example 1 and Comparative Example resulting from the decomposition of the hydrogen peroxide was measured by taking a digital image of the side of the tube using a camera. Image analysis software was used to measure the area of the picture covered by the tube. As the tube swells due to internal pressure exerted by oxygen gas, the area of the picture covered by the tube correspondingly increases.

Images were taken the day after dentifrice preparation and packaging (as a baseline measurement), and after ten days of 60° C. accelerated aging. The resultant images were scaled to the width of shoulder of the tube.

In a further test, the width of the tube was measured using calipers to determine the amount of tube expansion as a result of bloating. The tube width was measured the day after dentifrice preparation and packaging (as a baseline measurement), and after twenty one days of 60° C. accelerated aging.

Table 2 shows the increase in bloating as a function of time at 60° C. for the image analysis and caliper tests.

TABLE 2

|  | 10 days at 60° C. (% increase in bloating from baseline by image analysis) | 21 days at 60° C. (% increase in bloating from baseline by caliper analysis) |
| --- | --- | --- |
| Comparative Example 1 | 10 | 33 |
| Example 1 | 6 | 17 |

It may be seen that in Comparative Example 1 after 10 days aging there was greater increase in the imaged area of the tube as compared to Example 1, and also after 21 days aging there was greater bloating as measured by the caliper as compared to Example 1. In the caliper test, a 17% increase for Example 1 represented substantially no visually perceivable bloating when the tube was viewed with the human eye, whereas a 33% increase for Comparative Example 1 represented a slight to moderate visually perceivable bloating when the tube was viewed with the human eye.

These results indicate that the addition of the sodium acid pyrophosphate reduced hydrogen peroxide decomposition over the course of the accelerated aging tests. The addition of the sodium acid pyrophosphate provided that hydrogen peroxide had improved chemical stability in the accelerated aging test.

Then the physical stability of the dentifrices of Example 1 and Comparative Example 1 comprising hydrogen peroxide were evaluated.

To evaluate the physical stability of the dentifrice network, a sample of the respective dentifrice of Example 1 and Comparative Example 1 was subjected to accelerated aging at an elevated temperature at 49° C., and then the phase separation was evaluated to assess the solid/liquid phase separation which was determined using a visual scale of 0-4, a score of 0 representing no physical separation and a score of 4 representing a high degree of physical separation.

Table 3 shows the phase separation results after two accelerated aging periods of one month or two months at an elevated temperature at 49° C. for the dentifrices of Example 1 and Comparative Example 1.

TABLE 3

|  | 1 month at 49° C. Visual phase separation | 2 months at 49° C. Visual phase separation |
| --- | --- | --- |
| Comparative Example 1 | 2 | 4 |
| Example 1 | 0 | 2 |

It may be seen that in Comparative Example 1 there was greater visual phase separation of the dentifrice as compared to Example 1, for both test periods. The score of 2 represented an acceptable solid/liquid phase separation whereas a score of 4 represented an unacceptable solid/liquid phase separation.

These results indicate that the addition of the sodium acid pyrophosphate enhances the physical phase stability of the dentifrice compositions comprising hydrogen peroxide over the course of the accelerated aging tests. The addition of the sodium acid pyrophosphate provided that the dentifrice comprising hydrogen peroxide had improved physical stability in the accelerated aging test.

Examples 2 and 3 and Comparative Example 2

Sodium acid pyrophosphate can provide additional benefits in a dentifrice composition, for example reduced tooth surface staining, and in particular enhanced extrinsic stain prevention efficacy and stain removal efficacy.

Accordingly, dentifrice preparations having higher sodium acid pyrophosphate content as compared to Example 1 were prepared according to Examples 2 and 3, the compositions of which are specified in Table 4. Example 2 comprised 3 wt % sodium acid pyrophosphate and Example 3 comprised 5 wt % sodium acid pyrophosphate.

Apart from the additional sodium acid pyrophosphate content, the dentifrice of Examples 2 and 3 comprised similar compositions to the dentifrice of Example 1 except that in Examples 2 and 3 the thickener and viscosity modifier was crosslinked polyvinyl pyrrolidone rather than fumed silica and also there was a reduced amount of the calcium pyrophosphate abrasive. Furthermore, there was no phosphoric acid.

TABLE 4

| Ingredient | Example 2 | Example 3 | Comp. Ex. 2 |
|---|---|---|---|
| PEG$_{116}$/PPG$_{66}$ co-polymer | 7.5 | 7.5 | 7.5 |
| Glycerin | 26.56 | 24.56 | 22.56 |
| Propylene glycol | 20 | 20 | 20 |
| PEG 600 | 10 | 10 | 10 |
| Crosslinked PVP | 2.5 | 2.5 | 2.5 |
| Crosslinked PVP/H$_2$O$_2$ complex | 5.5 | 5.5 | 5.5 |
| Tetrasodium pyrophosphate (TSPP) | 2 | 2 | 2 |
| Sucralose | 0.05 | 0.05 | 0.05 |
| Sodium saccharin | 0.6 | 0.6 | 0.6 |
| Sodium monofluorophosphate | 0.76 | 0.76 | 0.76 |
| Sodium lauryl sulfate | 2 | 2 | 2 |
| Butylated hydroxytoluene (BHT) | 0.03 | 0.03 | 0.03 |
| Fumed silica | 2.5 | 2.5 | 2.5 |
| Flavor | 2 | 2 | 2 |
| Calcium pyrophosphate | 15 | 15 | 15 |
| Sodium acid pyrophosphate | 3 | 5 | 7 |
| Total | 100 | 100 | 100 |

The dentifrice compositions of Examples 2 and 3 and were tested to determine their viscosity after a two week storage period following preparation. The Brookfield viscosity was measured using Brookfield Model RVTDV-II with Spindle "E". The apparatus is calibrated and the spindle is brought to the surface of the paste. The spindle is run at 5 rpm and inserted into the paste. After 45 seconds, a Bku measurement (Brookfield units) is taken.

The results of this viscosity evaluation are described in Table 5 (below).

TABLE 5

| | Example 2 | Example 3 | Comparative Example 2 |
|---|---|---|---|
| Brookfield Viscosity (Bku) | 58 | 64 | >100 |

It may be seen that the dentifrices of Examples 2 and 3 had acceptable viscosity, in particular a Brookfield viscosity value of less than 65 Bku, which provides that these compositions are readily pumpable and extrudable.

Consequently, these results show that a sodium acid pyrophosphate content of up to 5 wt % provided acceptable viscosity in the dentifrice compositions.

As a comparison, a dentifrice composition having a still higher amount of sodium acid pyrophosphate was tested to determine viscosity properties.

The composition of Comparative Example 2 is also shown in Table 4, and included 7 wt % sodium acid pyrophosphate.

The pH and viscosity of the dentifrice of Comparative Example 2 were tested as for Examples 2 and 3 and the results are also shown in Table 5.

The dentifrice of Comparative Example 2 also exhibited an unacceptably high Brookfield viscosity of greater than 100, which meant that the composition was too viscous for the Brookfield viscometer to be able to test the composition.

Consequently, these results show that a sodium acid pyrophosphate content of greater than 5 wt % provided an unacceptably high viscosity in the dentifrice composition.

In summary, the data described in the Examples evidences the unexpected improvement in both the chemical stability of the peroxide whitening agent and the physical stability of the dentifrice incorporating such a peroxide whitening agent, and also the acceptable viscosity, when incorporating sodium acid pyrophosphate at up to 5 wt %, in accordance with the invention.

While particular embodiments of the invention have been illustrated and described, it will be obvious to those skilled in the art that various changes and modifications may be made without departing from the scope of the invention as defined in the appended claims.

The invention claimed is:

1. An oral care composition comprising (i) a peroxide whitening agent comprising a whitening complex of crosslinked polyvinylpyrrolidone complexed with hydrogen peroxide, (ii) sodium acid pyrophosphate (Na$_2$H$_2$P$_2$O$_7$) in an amount of from 0.1 wt % to 3 wt % based on the weight of the composition, and (iii) less than 3 wt % water based on the weight of the composition;
    and further comprising at least one humectant;
    wherein the at least one humectant comprises propylene glycol and glycerin, and wherein the composition comprises propylene glycol and glycerin in an amount of from 25 wt % to 60 wt % based on the weight of the composition; and
    further comprising 1 to 2 wt % tetrasodium pyrophosphate as an tartar control agent.

2. The composition of claim 1 wherein the composition is substantially anhydrous.

3. The composition of claim 1 wherein the whitening complex of crosslinked polyvinvlpyrrolidone complexed with hydrogen peroxide is present in an amount of from 0.5 wt % to 16.5 wt % based on the weight of the composition.

4. The composition of claim 3 wherein the whitening complex contains 10-30 wt % hydrogen peroxide and 5-15 wt % total nitrogen, based on the weight of the whitening complex.

5. The composition of claim 1 wherein the total amount of hydrogen peroxide is from 0.1 wt % to 3 wt % based on the weight of the composition.

6. The composition of claim 1 further comprising an abrasive selected from at least one of calcined alumina, silica, zirconium oxide, calcium pyrophosphate, dicalcium phosphate and precipitated calcium carbonate, or any mixture of two or more thereof.

7. The composition of claim 6 wherein the abrasive is present in an amount of from 5 wt % to 40 wt % based on the weight of the composition.

8. The composition of claim 7 wherein the abrasive is calcium pyrophosphate present in an amount of from 12 wt % to 37 wt % based on the weight of the composition.

9. The composition of claim 1 wherein the composition comprises propylene glycol in an amount of from 15 wt % to 30 wt % based on the weight of the composition and glycerin in an amount of from 5 wt % to 20 wt % based on the weight of the composition.

10. The composition of claim 1 further comprising an ethylene oxide, propylene oxide block co-polymer of average molecular weight greater than 5000 Da, being substantially free of an ethylene oxide, propylene oxide block co-polymer of average molecular weight less than 5000 Da.

11. The composition of claim 10 wherein the ethylene oxide, propylene oxide block co-polymer comprises (ethylene oxide)$_x$-(propylene oxide)$_y$, wherein x is an integer of 80-150 and y is an integer of 30-80.

12. The composition of claim 10 wherein the ethylene oxide, propylene oxide block co-polymer is present in an amount of from 5 wt % to 12 wt % based on the weight of the composition.

13. The composition of claim 1 further comprising polyethylene glycol of average molecular weight 400 to 800 Da.

14. The composition of claim 1 further comprising a thickening agent selected from crosslinked polyvinylpyrrolidone and fumed silica or a mixture thereof.

15. The composition of claim 14 wherein the thickening agent is present in an amount of from 1 wt % to 5 wt % based on the weight of the composition.

16. The composition of claim 1 comprising less than 2 wt % water based on the weight of the composition.

17. The composition of claim 1 which is a single phase composition.

18. The composition of claim 1, wherein the composition has a Bku value of less than 100.

19. A method of tooth whitening comprising applying the composition of claim 1 to the surface of a mammalian tooth.

* * * * *